United States Patent [19]
Davis

[11] Patent Number: 6,004,290
[45] Date of Patent: *Dec. 21, 1999

[54] URETHRAL SIZING CATHETER

[75] Inventor: Richard C. Davis, Tampa, Fla.

[73] Assignee: Urocath Corporation, Menlo Park, Calif.

[*] Notice: This patent is subject to a terminal disclaimer.

[21] Appl. No.: 08/986,190

[22] Filed: Dec. 5, 1997

Related U.S. Application Data

[62] Division of application No. 08/674,722, Jul. 2, 1996, Pat. No. 5,718,686.

[51] Int. Cl.$^6$ ............................ A61M 29/00; A61M 31/00
[52] U.S. Cl. .......................... 604/96; 604/517; 604/101; 604/500
[58] Field of Search ................. 604/96, 97, 99, 604/101, 103, 104, 105, 327, 328, 349, 352, 49, 50, 500, 503, 514, 54, 517; 128/898; 606/192, 198

[56] References Cited

U.S. PATENT DOCUMENTS

| | | | |
|---|---|---|---|
| 4,211,233 | 7/1980 | Lin | 128/349 |
| 4,350,161 | 9/1982 | Davis, Jr. | 128/349 |
| 4,423,725 | 1/1984 | Baran et al. . | |
| 4,432,757 | 2/1984 | Davis, Jr. . | |
| 4,676,228 | 6/1987 | Krasner et al. . | |
| 4,932,938 | 6/1990 | Goldberg et al. | 604/96 |
| 4,932,956 | 6/1990 | Reddy et al. | 606/192 |
| 4,946,449 | 8/1990 | Davis, Jr. | 604/256 |
| 5,002,558 | 3/1991 | Klein et al. | 606/192 |
| 5,112,306 | 5/1992 | Burton et al. . | |
| 5,242,398 | 9/1993 | Knoll et al. . | |
| 5,419,763 | 5/1995 | Hildebrand . | |
| 5,588,965 | 12/1996 | Burton et al. . | |
| 5,718,686 | 2/1998 | Davis | 604/101 |
| 5,785,641 | 7/1998 | Davis | 600/30 |
| 5,785,694 | 7/1998 | Cohen et al. | 604/250 |

FOREIGN PATENT DOCUMENTS

| | | | |
|---|---|---|---|
| 79314/91 | 1/1992 | Australia | 604/96 |

*Primary Examiner*—Ronald K. Stright, Jr.
*Assistant Examiner*—Patricia M. Bianco
*Attorney, Agent, or Firm*—Griffin, Butler, Whisenhunt & Szipl, LLP

[57] ABSTRACT

An anchoring system for a urethral catheter (14, 36), and a method of its use, involve a resilient anchor-interval portion (40) of a catheter drainage shaft (42, 42'), positioned between a bladder balloon (26) and a urethral anchoring cuff balloon (44). The anchor-interval portion has a sinusoidal configuration lengthwise thereof which provide a proper linear elastic resilience for allowing the bladder balloon and the urethral anchoring cuff balloon to be separated a substantial distance for impinging against what remains of a prostate gland (20, 28, 32).

19 Claims, 1 Drawing Sheet

URETHRAL SIZING CATHETER

This is a division of application Ser. No. 08/674,722, filed Jul. 2, 1996, now U.S. Pat. No. 5,718,686.

BACKGROUND OF THE INVENTION

This invention relates to urethral catheters and more specifically to systems and methods for anchoring such catheters in urethras.

An example of a urethral catheter of the type to which this invention relates is a catheter disclosed in U.S. Pat. No. 4,350,161 to Richard C. Davis, Jr. In the catheter disclosed in that patent there is a valve which, when the catheter is properly anchored in the patient's urethra, can be activated by application of an external force. That catheter is designed so that when it is installed its downstream tip does not extend beyond a penile meatus in any patient position. As is set forth in U.S. Pat. No. 4,350,161 of Richard C. Davis, Jr., a method of inserting such an indwelling urethral catheter includes the step of determining the length of the patient's urethral tract. Thus, since the advent of the indwelling urethral catheter of the type described above, proper sizing of the catheter has been appreciated as a critical element in a protocol for positioning the device and in its proper functioning.

During development of this catheter it has come to be better appreciated that as the bladder fills and empties and the body moves, the bladder and urethra shift and stretch relative to one another. It has been determined that overall urethral length is generally shortest when a patient is lying down and lengthens when the patient is sitting or standing. Thus, it has been determined that a properly sized male indwelling urethral catheter of this type must be short enough to remain totally inside the patient's urethra in all positions, but yet long enough to allow easy access the valve located in the patient's urethra for voiding and for removal of the catheter itself.

If it is sized too long, the catheter may occasionally protrude from the tip of the penis, potentially causing pain, swelling, and infection. If the catheter is too short, the patient may not be able to easily access the valve to properly actuate it. Further, the patient may have difficulty removing the catheter.

Another feature of the indwelling urethral catheter described in U.S. Pat. No. 4,350,161 to Richard C. Davis, Jr. is that it includes not only a bladder balloon but also an anchoring urethral cuff balloon along a catheter drainage shaft for inflating in the patient's urethra. A primary purpose of the urethral anchoring cuff balloon, as was described in U.S. Pat. No. 4,350,161, is to prevent retrograde movement of the catheter into the bladder by using the prostatic urethra as a buttress against which the urethral anchoring cuff balloon is juxtaposed.

To meet different lengths of normal adult urethral tracts, indwelling urethral catheters of the type of this invention, have been, to date, manufactured in six different overall lengths so that most any length of an adult male penis and urethral tract can be accommodated. However, notwithstanding this, sizing problems have continued to be encountered. In this regard, until recently, an indwelling urethral catheter of the type of this invention was fitted to a patient by first placing a measuring catheter, having a bladder balloon and drainage shaft extending beyond the patient's penile meatus, in the patient. By noting the position of the penile meatus along the measuring catheter's drainage shaft, with the patient in various positions, the overall length of the patient's urethral tract was determined. An indwelling urethral catheter was then chosen from the six different lengths corresponding to the overall length of the patient's urethral tract. Using this method, however, problems have continually been encountered in choosing the proper length catheters. That is, after catheters, whose lengths were determined as described above, have been installed it has been found that they often have not remained in their preferred positions. As the body accommodates to the presence of the device in some cases they have shifted downstream to extend beyond a patient's penile meatus when the patient was in a lying position and in other cases they have shifted upstream so far from the meatus that the patient has not been able to activate the valve to urinate. Because of this, it has sometimes been necessary to try various size catheters in a patient, one after the other—even though the patient was previously measured—until a catheter of the correct size, if ever, was found. Thus, in many cases, catheter sizes have actually been determined as much by trial and error as by measuring, if at all. Such trial and error has resulted in discomfort for patients and has proven to be expensive, since it has resulted in the expenditure of many catheters and much time and effort; and often patients were not able to be fitted at all.

The problem has been that some inserted prior-art indwelling urethral catheters, of the type of this invention, have experienced undue relative linear movement along urethral tracts. That is, sometimes they have appeared to be in their correct positions but then at other times they have moved linearly, within the urethral tract, to inappropriate positions. Thus, when some catheters were initially sized using the above-described method, which relied solely on the bladder-to-meatus length, they were occasionally noted to shift downstream in the urethra; thereby appearing to be "too long", and their tips intermittently protruded from the penile meatus. It has been assumed that such shifting represented "device failure"; presumably the bladder balloon had leaked thus allowing downstream migration. An opposite situation has been noted in some patients who at first could easily access their valves but who, over time, had increasing difficulty accessing their valves because their catheters migrated upstream. Again, this was previously interpreted as a "device failure" whereby the urethral anchoring cuff balloon was thought to have deflated allowing such upstream migration.

It has now been realized that the distance between the bladder neck orifice and the bulbous urethra, which shall be referenced herein as the "interballoon urethral segment length" and as the "prostatic urethral length", varies tremendously among patients. Such a difference in interballoon urethral segment lengths is illustrated in FIG. 3 where are shown diagrammatically: a patient's bladder 10, the patient's penis 12, and a urethral sizing catheter 14 extending through a urethral tract 16 from the bladder 10 to beyond a penile meatus 18. For purposes of illustration, three different size interballoon urethral segment lengths (i.e. prostate gland or prostate Fossa as the case may be) are represented diagrammatically on FIG. 3. It should be understood that individual patients will have only one of these interballoon urethral segment lengths; however, all three are depicted on FIG. 3 so that a reader can compare the different size interballoon urethral segment lengths with interballoon spacings (balloon spacings).

A normal-size prostate gland 20 has a downstream side 22 which is located approximately four centimeters from the interior surface of a bladder neck orifice 10a (or downstream side 24 of a bladder balloon 26). This four centimeter spacing is represented by the letter "b" in FIG. 3. However, an enlarged, or hypertrophic prostate gland 28 has a downstream side 30 which is spaced approximately 5.5 cm from the downstream side 24 of the bladder balloon 26 in the bladder 10. This 5.5 cm measurement is signified by the letter "a" in FIG. 3. Finally, a post prostatectomy prostatic Fossa 32, which is essentially what is left when a prostate is removed (or at least diminished), has a downstream side 34 which is spaced approximately 2.0 cm from the downstream side 24 of the bladder balloon 26 when it is in the bladder 10. This downstream side of the bladder balloon 26 can also be influenced to some extent by the position of a bulbous urethra 68. In this regard, when a patient's prostate is removed, it sometimes happens that some of the bladder must also be removed and reconstructed. In this process, these elements move relative to one another to some extent.

In any event, this 2.0 cm measurement is indicated by the letter "c" in FIG. 3. It should be understood that these measurements are only given as approximations and that they can vary significantly from patient to patient. However, it can be seen from these approximations, in FIG. 3, that the relative interballoon urethral segment lengths ("b", "a", and "c") of patients—and thus necessary catheter balloon spacings—can vary by a factor of nearly three (comparing "a" with "c").

It has been suggested that both urethral sizing catheters and indwelling urethral catheters be manufactured in sets, with the catheters of each set having approximately the same length, but each catheter of the set having different balloon spacings to accommodate the different interballoon urethral segment lengths (a, b, c). Under this system, it has been anticipated that up to 18 different indwelling urethral catheter sizes will be necessary, with there being six different overall clinical catheter lengths, but at least three different balloon spacings for each overall clinical catheter length. Further, it is anticipated that at least three urethral sizing catheters will be necessary.

Although the system of these many different catheters solves the problem of the various interballoon urethral segment lengths, it is expensive to manufacture so many different-size catheters.

Thus, it is an object of this invention to provide an anchoring system for an indwelling urethral catheter and, possibly for a urethral sizing catheter, which accommodates various interballoon urethral segment lengths so that a single catheter can be used with various interballoon urethral segment lengths.

Similarly, it is an object of this invention to provide a method of anchoring a urethral catheter which accommodates substantial differences in urethral anatomies.

SUMMARY OF THE INVENTION

According to principles of this invention, an anchoring system for a urethral catheter, and a method of its use, involve the use of a resilient anchor-interval portion of a catheter drainage shaft between a bladder anchoring member and a urethral anchoring member which affords a stretching action to occur between the bladder and urethral anchoring members for allowing them to separate and to then thereafter bias against bases of the bladder and the bulbous urethra respectively. Thus, the bladder anchoring member and the urethral anchoring member impinge against prostatic tissue located between the bladder and the bulbous urethra.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

According to this invention, an indwelling urethral catheter 36 and/or possibly a urethral sizing catheter 14, have a special anchoring system 38 thereon.

Figure 3:
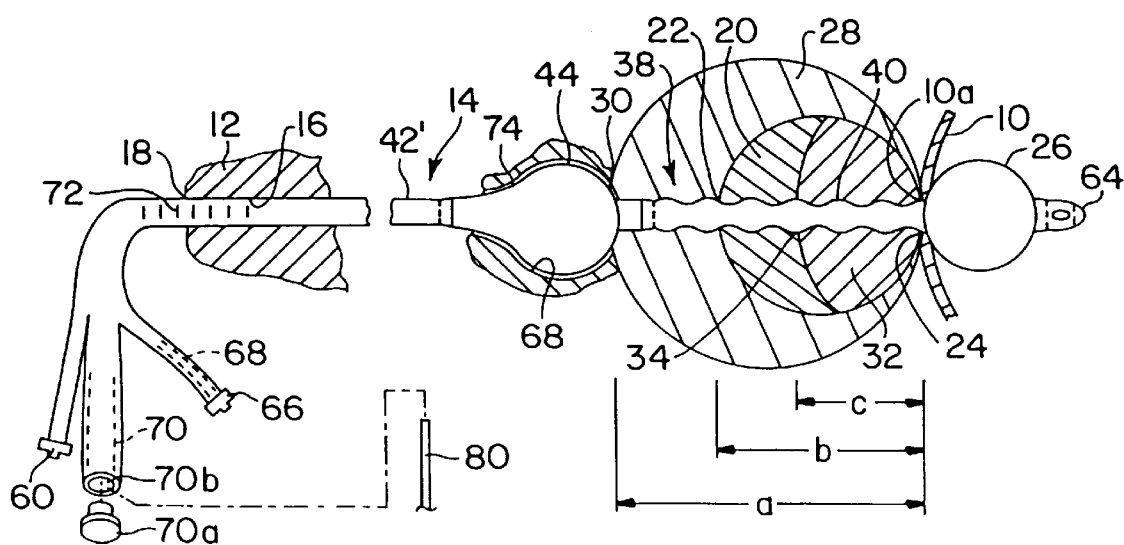

Basically, the anchoring system 38 comprises a resilient anchor-interval portion 40, of a catheter drainage shaft 42 (42' for sizing catheter of FIG. 3), positioned between the bladder balloon 26 and a urethral anchoring cuff balloon 44. The anchor-interval portion 40 has a proper resilience for stretching to allow the bladder balloon 26 and the urethral anchoring cuff balloon 44 to separate a substantial distance, as is depicted in FIG. 3, and for thereafter biasing the bladder balloon 26 and the urethral anchoring cuff balloon 44 toward one another for impinging against prostatic tissue located between the base of the bladder 10 and the urethral anchoring cuff balloon 44. As used herein, the term "prostatic tissue" refers not only to tissue forming the prostate gland, but also surrounding tissue and tissue positioned where a prostate gland would normally be located. This definition is necessary because when a prostate gland has been removed the balloons may not actually be impinging on tissue that was part of the prostate gland, but rather on surrounding tissue, scar-tissue, replacement tissue and the like.

Figure 2:
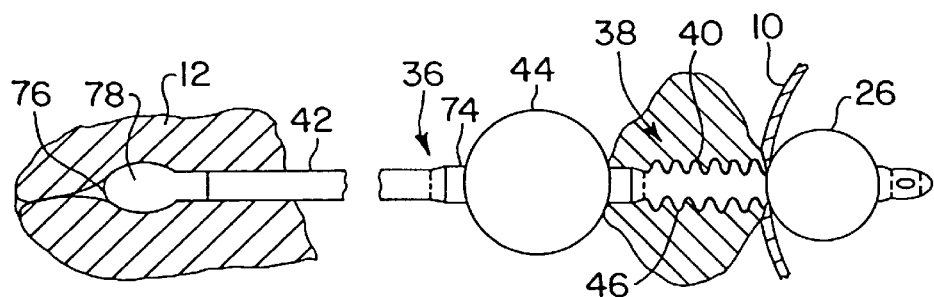
FIG. 2 is a segmented, side view of an indwelling urethral catheter of this invention when mounted in a urethra, with a portion of a penis and a portion of a prostate gland being shown in cross-section; and, FIG. 3 is a schematic side view, partially-exploded, of a sizing catheter employing principles of this invention, with a portion of a penis and various prostate glands being shown schematically thereon for illustration.

Such a structure of the anchoring system 38 allows the bladder balloon 26 and the urethral anchoring cuff balloon 44 to oppositely impinge against any size prostate 20, 28, or 32. Thus, the anchoring system of this invention, and its method of use, allows, within certain limits, all sizing and indwelling urethral catheters 14 and 36 to have essentially the same balloon configuration for fitting virtually all shapes and sizes of prostate glands. FIG. 2 shows the anchoring system 38 mounted in a prostatic Fossa following a prostate removal operation, in which the anchor interval portion 40 is tensioned only slightly. On the other hand, the same type anchoring system 38 shown on the urethral sizing catheter 14 of FIG. 3 is in an extended, or almost fully tensioned, configuration for mounting the urethral sizing catheter 14 in a patient having a hypertrophic prostate gland 28. In this regard, the anchor-interval portion 40 is constructed to have a corrugated wall 46. The wall 46 is molded with a mold 48 and a mandrel 50. The wall 46 is constructed of a medicalgrade silicone rubber 52. An interior surface 54 of the mold 48 and an exterior surface 56 of the mandrel 50 have mating sinusoidal shapes in a longitudinal direction, but are round in a plane perpendicular to the longitudinal direction. Thus, the wall 46 is formed to have the corrugated shape depicted in FIG. 2.

Figure 1:
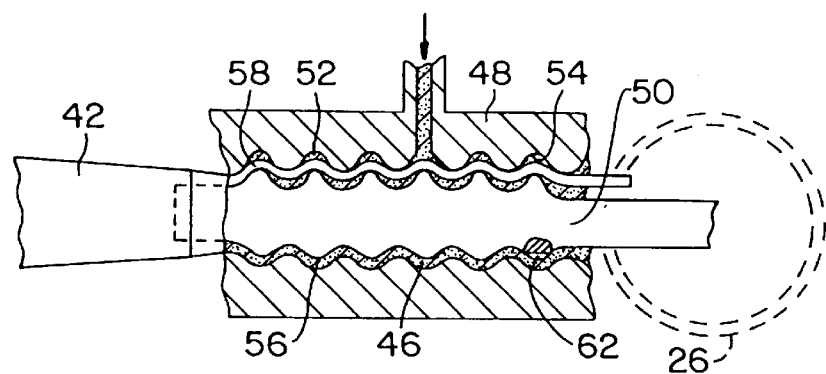
FIG. 1 is a segmented, enlarged, side sectional schematic view of a mold during a step of molding an anchor-interval portion of a urethral catheter of this invention, with some elements being shown schematically in dashed lines.

During the molding of the wall 46, an inflation-lumen tube 58 is placed in a notched groove which runs longitudinally in the space between the mold 48 and the mandrel 50 so as to be fixedly held and molded into the wall 46. The inflation-lumen tube 58 is also formed of silicon rubber to become an integral part of the wall 46. A bore, or lumen, of the inflation-lumen tube 58 is used to inflate the bladder balloon 26. An upstream end of the lumen formed by the inflation-lumen tube 58 communicates with the bladder balloon 26 and a downstream end of the lumen formed by the inflation-lumen tube 58 communicates with a Roberts valve 60, as will be described below with reference to operation of the device. Either the mold 48 or the mandrel 50, or both, can have angularly-spaced niches 62 on their surfaces for holding the inflation-lumen tube 58 in a desired angular position. The nitch 62 depicted in FIG. 1 is not at the inflation-lumen tube 58 for purposes of clearer illustration. However, it should be understood that the inflation-lumen tube 58 would fit in the niches 62 to ensure that the inflation-lumen tube 58 does not bow circumferentially but rather follows the longitudinal sinusoidal corrugations of the wall 46. Likewise, in another embodiment, a second inflation lumen tube may be situated oppositely yet similarly as the inflation-lumen tube 58. Such a second inflation lumen tube, would be used to communicate with and to inflate the urethral anchoring cuff balloon 44 via its connection to an external inflating device which can be frangibly attached to the downstream end of the urethral catheter 36 of FIG. 2 or alternately to the Roberts valve 60 of the sizing catheter 14 of FIG. 3. In this embodiment the exterior length of both the sizing catheter 14 and the indwelling urethral catheter 36 would probably be molded at once.

The anchor interval portion 40 can be molded, as depicted in FIG. 1, directly to adjacent portions of the catheter drainage shaft 42, 42'. Once the anchor interval portion 40 has cured, the mold 48 is opened and the mandrel 50 is removed. Of course, manufacturing procedural steps could be carried out in various sequences and in manners other than as is described above.

In use, once it is determined that a patient is a candidate for the indwelling urethral catheter 36, he is first fitted using a urethral sizing catheter. Currently, it is thought that the urethral sizing catheter used to fit the patient should have a fixed-length anchor interval portion 40, and not a resilient anchor interval portion as is depicted in FIG. 3. In order to do that, the patient must be examined to determine the approximate size of his prostate and a sizing catheter must then be chosen having a balloon spacing corresponding to the size of the prostate gland. Such a system is described in a previous patent application by Richard C. Davis. However, it might also be possible to use the sizing catheter depicted in FIG. 3 hereof. If the sizing catheter of FIG. 3 were used, it might not be necessary for an investigator to determine the size of the patient's prostate gland, inasmuch as the anchor interval portion 40 will accommodate to virtually all prostate gland sizes and shapes, as is depicted in FIG. 3 and as was described above.

Basically, if the sizing catheter of FIG. 3 were used, the operator applies an anesthetic lubricant to the urethral sizing catheter 14 and then inserts a lubricated, rigid, yet flexible guide wire 80 (FIG. 3) through the entire extent of a drainage lumen 70, beginning at drainage lumen orifice 70b until a tip of the guide wire impinges on a hollow depression of the Murphy eye tip 64. The operator then advances the guide wire against a resistance applied by the anchor internal portion 40, thus effectively straightening the resilient sinusoidal shape therein so that the anchor interval portion 40 has approximately the shape shown in FIG. 3. and inserts the straightened catheter, Murphy tip 64 first, into the patient's bladder through the patient's urethral meatus 18. The bladder balloon 26 is inflated with a volume of sterile saline solution through an inflation valve 66 and an inflation lumen 68. It should be understood, that the inflation lumen 68 communicates with a bore, or lumen, of the inflation-lumen tube 58 that was molded into the anchor interval portion 40 as is depicted in FIG. 1. Thereafter:

1. A gentle external axial traction is applied to the catheter to snug the bladder balloon 26 against a base of the bladder neck orifice boa and the guide wire is withdrawn. Axial traction is then applied to the Roberts valve end of the sizing catheter to extend the anchor interval portion 40.

2. While applying this continual axial traction, a volume of sterile saline is instilled through the inflation Roberts valve 60, thus partially inflating the urethral anchoring cuff balloon 44 in the patient's bulbous urethra 68. As this is done, the tension placed on the catheter is released and the urethral anchoring cuff balloon 44 is retracted in an upstream direction along the urethra, by the elastic resilience of the anchor interval portion 40, toward the prostatic tissue (28, 20 or 32) thus fully seating the urethral anchoring cuff balloon 44 into the patient's bulbous urethra. One can feel the urethral anchoring cuff slide into position in the bulbous urethra. The urethral anchoring cuff balloon is then finally filled to a point of mild discomfort for the patient. While the urethral anchoring cuff balloon 44 is being inflated, it will impinge against the prostate gland, (or what is left thereof) 20, 28 or 32. In other words, the anchor interval portion 40 expands so that the bladder balloon 26 and the urethral anchoring cuff balloon 44 are positioned on opposite sides of the prostatic tissue but biases these two balloons against opposite sides of the prostatic tissue. An operator can control to some degree the position of the graduated indicia 72 along the sizing catheter drainage shaft 42', relative to the penile meatus 18, by varying the amount of fluid placed in the urethral anchoring cuff balloon 44.

3. The bladder 10 is then slowly instilled with a volume of sterile saline through a drainage-filling lumen 70 of the urethral catheter 14. The drainage lumen is then occluded with a plug 70a (shown schematically) and the patient is observed for a few minutes up to as long as several days. In some cases, it is necessary to fill and void bladders a number of times in order to condition patients who have not had full bladders for a long time, for example.

4. Once the patient is able to tolerate the urethral sizing catheter 14 with a full bladder, without discomfort, leakage, spasms or other difficulties, the operator reads and notes the patient's overall clinical urethral length from graduation indicia 72 located on an external surface of the urethral sizing catheter 14 which extends beyond the penile meatus 18 when the patient is in prone, sitting, and standing positions, with little or no traction applied to the catheter. If any difficulties in the patient are noted, adjustment in balloon volumes can be made to "custom-fit" the size for a given patient. The volumes used for inflating the balloons for achieving particular graduation-indicia readings are also noted. The urethral sizing catheter is then removed (after voiding the bladder) by deflating the bladder balloon 26 and the urethral anchoring cuff balloon 44 and the urethral sizing catheter is withdrawn from the patient's penis by applying gentle axial traction.

5. An indwelling urethral catheter 36 is then selected having an appropriate catheter drainage shaft 42 length from a downstream side 74 of the urethral cuff balloon 44 to a downstream end 76 of the catheter drainage shaft 42 such that when the indwelling urethral catheter 36 is inserted and anchored in the patient, its downstream end 76 is inset from the penile meatus 18, as is depicted in FIG. 2. But yet, its downstream tip 76 (and an evacuation valve 78 located near the downstream tip 76) are relatively close to the penile meatus in appropriate positions of the patient.

6. The indwelling urethral catheter 36 that has been selected is then inserted in the same manner as discussed above for the sizing catheter, but with the use of a drainage/inflation device as is described in U.S. Pat. No. 4,932,938 to Goldberg et al. and U.S. Pat. No. 4,946,449 to Davis (description not included herein for purposes of simplicity), and its bladder balloon 26 and urethral anchoring cuff balloon 44 are inflated sequentially in that order with the identical volumes as were determined by the sizing catheter. Again, once the bladder balloon is inflated, the anchor interval portion is stretched by applying tension. The cuff balloon is inflated and allowed to find its "seat" in the bulbous urethra.

It can be appreciated by those of ordinary skill in the art that for purposes of sizing a patient for an indwelling urethral catheter 36, an important measurement of the urethral tract is a distance from the inflated urethral anchoring cuff balloon 44 to the downstream end 76 of the catheter drainage shaft 42. That is, when the urethral anchoring cuff balloon 44 is inflated, it will find its proper location (and it is allowed to do this by the resilient anchor interval portion 40), within the bulbous urethra 68. Although the graduated indicia 72 of the urethral sizing catheter 14 generally indicates the clinical length of the urethral tract, this indicia also indicates the distance between the penile meatus 18 and the downstream side of the urethral anchoring cuff balloon 44.

It will also be appreciated by those of ordinary skill in the art that, generally, all urethral sizing catheters 14 and indwelling urethral catheters 36 need only have one anchoring system 38, with the urethral anchoring cuff balloon 44, the anchor interval portion 40, and the bladder balloon 26 being essentially identical for each. Also, generally, a single urethral sizing catheter 14 can be used for all patients. However, there must be a set of indwelling urethral catheters 36, with each catheter of the set having a different length from the downstream end of the urethral anchoring cuff balloon 44 to the downstream end of the valve end 76.

Notwithstanding what is said in the previous paragraph, it might be necessary to employ different anchoring systems for patients who differ greatly in size (such as adults and children).

Also, notwithstanding the above, it is presently thought that it may be best to use sizing catheters which do not have the resilient anchor interval portion of this invention. That is, at the present, it appears that sizing catheters should have fixed anchor interval portions 40, in which case it would be necessary to have at least three sizing catheters, each with a different balloon spacing. Thus, it is anticipated that the preferred use of the anchoring system of this invention is for indwelling urethral catheters, generally shown in FIG. 2. However, additional clinical data must be obtained.

It is anticipated that at least three different lengths of indwelling urethral catheters will be required.

An important aspect of this invention is that it automatically accommodates to various prostate sizes and shapes.

This invention makes possible an indwelling urethral catheter which has a general application. That is, one need not manufacture nor stock so many different indwelling urethral catheters as was previously the case.

While the invention has been particularly shown and described with reference to a preferred embodiment, it will be understood by those skilled in the art that various changes in form and detail may be made therein without departing from the spirit and scope of the invention.

What is claimed as being novel in this invention is:

1. An urethral sizing catheter comprising:
    a catheter drainage shaft, defining an enclosed drainage canal through which urine can flow, for extending through and being anchored in, the urethra so that an upstream end is positioned in a patient's bladder and a downstream-most end extends beyond a urethral meatus;
    an anchoring system mounted on said drainage shaft for anchoring said drainage shaft in said urethra for preventing downstream and upstream migration of said drainage shaft, said anchoring system including;
    a bladder anchoring member mounted at the upstream end of said catheter drainage shaft for engaging said bladder and thereby contacting a bladder wall for deterring downstream migration of said catheter drainage shaft in said urethra; and,
    an urethral anchoring member mounted on said catheter drainage shaft at a position spaced downstream of said bladder anchoring member for distending in said urethra for preventing upstream migration of said catheter drainage shaft in said urethra;
    wherein an anchor-interval portion of said catheter drainage shaft, positioned between said bladder anchoring member and said urethral anchoring member, has an elastic resilience for allowing said bladder and urethral anchoring members to separate a substantial distance and for thereafter biasing the bladder and urethral anchoring members toward one another for impinging against opposite sides of prostatic tissue located between the bladder and urethral anchoring members.

2. The urethral sizing catheter as in claim 1 wherein said catheter drainage shaft comprises graduated indicia.

3. The urethral sizing catheter as in claim 2 wherein said graduated indicia extend from upstream of a urethral meatus to downstream of the urethral meatus.

4. The urethral sizing catheter as in claim 1 wherein said bladder and urethral anchoring members are balloons.

5. The urethral sizing catheter as in claim 1 wherein said anchor-interval portion has a corrugated lengthwise cross-section.

6. The urethral sizing catheter as in claim 1 wherein said anchor-interval portion is of a size so that said bladder and urethral anchoring members will be biased against opposite sides of prostatic tissue.

7. The urethral sizing catheter as in claim 1 wherein said urethral sizing catheter is a male urethral sizing catheter and wherein said catheter drainage shaft has a length such that its downstream-most end lies downstream of a penile meatus.

8. A method of anchoring a urethral sizing catheter comprising the steps:
    providing a catheter drainage shaft having an expandable bladder anchoring member at an upstream end portion thereof and an expandable urethral anchoring member mounted on said catheter drainage shaft downstream of said expandable bladder anchoring member, wherein an anchoring interval portion of said catheter drainage shaft, between said expandable bladder anchoring member and said expandable urethral anchoring member is substantially resilient for allowing said expandable bladder anchoring member and said expandable urethral anchoring member to be linearly distanced from one another and for thereafter applying a bias to said expandable bladder anchoring member and said expandable urethral anchoring member for retracting said expandable bladder anchoring member and said expandable urethral anchoring member linearly toward one another;

mounting said urethral sizing catheter in a urethra by distending said expandable bladder anchoring member in the patient's bladder and the expandable urethral anchoring member in the patient's bulbous urethra and thereby causing said expandable bladder anchoring member and said expandable urethral anchoring member to separate from one another while stretching said anchoring interval portion so that said anchoring interval portion biases said expandable bladder anchoring member and said expandable urethral anchoring member against opposite sides of tissue.

9. A method as in claim 8 wherein the step of providing a catheter drainage shaft includes the substep of making said anchor interval portion to have a corrugated shape.

10. A method as in claim 8 wherein is further included the step of inserting a guide wire in the drainage shaft for extending the anchoring interval portion before said urethral sizing catheter is mounted in said urethra.

11. A method as in claim 8 wherein the expandable bladder anchoring member is a bladder balloon and the expandable urethral anchoring member is a urethral anchoring cuff balloon.

12. A method for fitting a male patient with an indwelling urinary catheter having an expandable urethral anchoring member and a downstream end which comprises the steps of:

measuring a partial urethra distance from a bulbous urethra of a patient to a penile meatus of the patient by mounting a urethral sizing catheter in the patient's urethra by distending a sizing expandable urethral anchoring member of the urethral sizing catheter in the patient's bulbous urethra, with the sizing catheter extending out of the patient's urethral meatus and then choosing an indwelling urinary catheter with a length from an indwelling expandable urethral anchoring member of the indwelling urinary catheter for being expanded in the bulbous urethra to a downstream end of the indwelling catheter being slightly less than said partial urethra distance measured with said urethral sizing catheter.

13. The method of claim 12, wherein said urethral sizing catheter has no expandable anchoring member a fixed distance upstream of said sizing expandable urethral anchoring member.

14. The method of claim 12, wherein said urethral sizing catheter comprises:

a catheter drainage shaft, defining an enclosed drainage canal through which urine can flow, for extending through and being anchored in, the urethra so that an upstream end is positioned in a patient's bladder and a downstream-most end extends beyond the urethral meatus;

an anchoring system mounted on said drainage shaft for anchoring said drainage shaft in said urethra for preventing downstream and upstream migration of said drainage shaft, said anchoring system including;

a bladder anchoring member mounted at the upstream end of said catheter drainage shaft for engaging said bladder and thereby contacting a bladder wall for deterring downstream migration of said catheter shaft in said urethra; and, an urethral anchoring member mounted on said catheter drainage shaft at a position spaced downstream of said bladder anchoring member for distending in said urethra for preventing upstream migration of said catheter drainage shaft in said urethra;

wherein an anchor-interval portion of said catheter drainage shaft, positioned between said bladder anchoring member and said urethral anchoring member, has an elastic resilience for allowing said bladder and urethral anchoring members to separate a substantial distance and for thereafter biasing the bladder and urethral anchoring members toward one another for impinging against opposite sides of prostatic tissue located between the bladder and urethral anchoring members.

15. The method of claim 12, wherein said urethral sizing catheter comprises graduated indicia positioned at the penile meatus for defining a length to the penile meatus when the expandable urethral anchoring member is expanded in the patient's bulbous urethra, and said indwelling urinary catheter is chosen to have a length shorter than the length defined to the penile meatus.

16. The method of claim 12, conducted in the absence of a determination of the size of the patient's prostate gland.

17. The method of claim 12, wherein said expandable urethral anchoring member is a cuff balloon.

18. A method for determining a partial urethra distance of a patient which comprises the steps of inserting a urethral sizing catheter assembly comprising an expandable bladder anchoring member, an expandable urethral anchoring member, a resilient anchor interval portion, and length indicia, into a patient's bladder through a patient's urethral meatus, expanding the expandable bladder anchoring member of said catheter assembly, applying axial traction to said catheter assembly in order to snug the expandable bladder anchoring member against a base of a bladder orifice of the patient and in order to extend the anchor interval portion, continuing to apply axial traction to said catheter assembly while partially expanding the expandable urethral anchoring member, releasing axial traction to permit elastic resilience of the anchor interval portion to retract the expandable urethral anchoring member, and reading the patient's partial urethra distance from the indicia located on the urethral sizing catheter.

19. The method of claim 18, wherein said expandable bladder anchoring member is a bladder balloon and said expandable urethral anchoring member is a cuff balloon.

* * * * *